United States Patent [19]
Popovic et al.

[11] Patent Number: 6,119,536
[45] Date of Patent: Sep. 19, 2000

[54] CONSTANT DISTANCE CONTACTLESS DEVICE

[75] Inventors: Zoran D. Popovic, Mississauga; Philip D. Waldron, Whitby, both of Canada

[73] Assignee: Xerox Corporation, Stamford, Conn.

[21] Appl. No.: 08/961,436

[22] Filed: Oct. 30, 1997

[51] Int. Cl.[7] .......................... G01M 19/00; G01N 21/17; G01N 27/24; G01N 27/61

[52] U.S. Cl. .......................... 73/866.5; 137/342; 324/456; 324/690; 356/237.2

[58] Field of Search .......................... 73/866.5; 137/342; 324/690, 456, 457, 458; 356/237.2

[56] References Cited

U.S. PATENT DOCUMENTS

| | | | |
|---|---|---|---|
| 3,898,001 | 8/1975 | Hardenbrook et al. | 324/72 |
| 4,134,137 | 1/1979 | Joacobs et al. | 358/293 |
| 4,233,384 | 11/1980 | Turner et al. | 430/58.75 |
| 4,265,990 | 5/1981 | Stolka et al. | 430/58.8 |
| 4,299,897 | 11/1981 | Stolka et al. | 430/58.8 |
| 4,306,008 | 12/1981 | Pai et al. | 430/58.8 |
| 4,439,507 | 3/1984 | Pan et al. | 430/58.8 |
| 4,450,489 | 5/1984 | Barry et al. | 358/348 |
| 5,175,503 | 12/1992 | Mishra et al. | 324/457 X |
| 5,703,487 | 12/1997 | Mishra | 324/456 |
| 6,008,653 | 12/1999 | Popovic et al. | 324/456 |

OTHER PUBLICATIONS

Zoran Popovic, Dave Parco, Pablo Iglesias, "Nature of Microscopic Electrical Defects in organic Photoreceptors", proceedings SPIE–SPSE Electronic Imaging Science and Technology Symposium, Feb. 11–16, 1990, Santa Clara, Calif.

Zoran Popovic, Pablo Iglesias, "Characterization of Microscopie Elelectrical Non–Uniformities in Xerographic Photoreceptors", Fifth International Congress on Advances and Non–Impact printing Technologies, Nov. 12–17, 1989, San Diego, Calif. pp. 11–14.

R. Gerhard–Multhaup and W. Perry, J. Phys. E; Sci. Instrum. 16, 421–422 (1983) High–Resoloution Probing of Surface–Charge Distributions in Electret Samples. Month not given.

E.J. Yarmchuck and G.E. Keefe, J. Appl. Phys 66 (11), Dec. 1, 1989 pp. 5435–5439 High–Resolution Surface Charge Measurements on a Organic Photoconductor.

*Primary Examiner*—Thomas P. Noland

[57] ABSTRACT

A contactless system including an aerodynamically floatable device, a member having an outer surface adjacent to and spaced from the aerodynamically floatable device, a support mechanism adapted to support the aerodynamically floatable device for free movement toward and away from the outer surface of the member, the aerodynamically floatable device having a side adjacent to, spaced from, parallel to and facing the outer surface of the member, the aerodynamically floatable device also containing at least one passageway for directing at least one stream of a gas from the side of the aerodynamically floatable device toward the outer surface of the member with sufficient pressure to maintain the aerodynamically floatable device a constant distance from the outer surface of the member. This system may be utilized in a process comprising providing an aerodynamically floatable device spaced from an outer surface of a member, the aerodynamically floatable device being at least moveable toward and away from the outer surface of the member, the aerodynamically floatable device comprising at least one passageway for directing at least one stream of a gas from the moveable device toward the outer surface of the member, flowing a gas through the passageway with sufficient pressure to maintain the aerodynamically floatable device a constant distance from the outer surface of the member.

29 Claims, 9 Drawing Sheets

FIG. 12
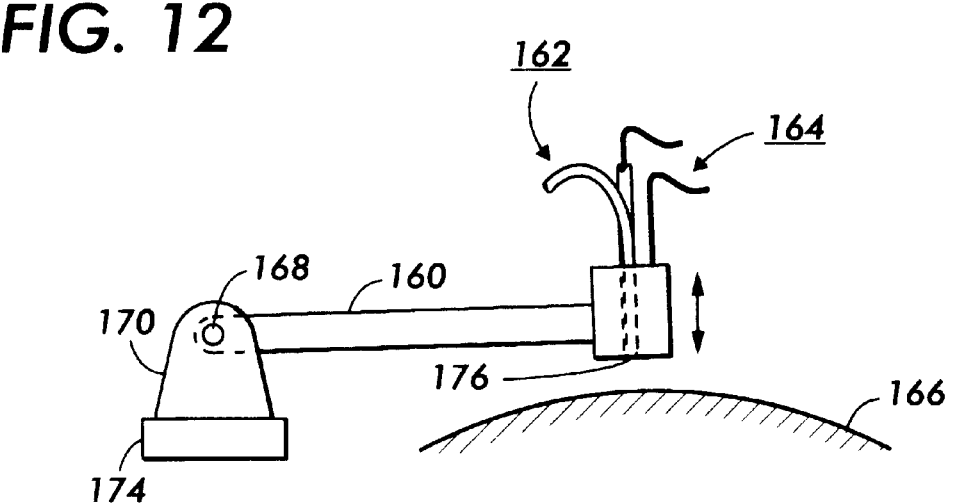
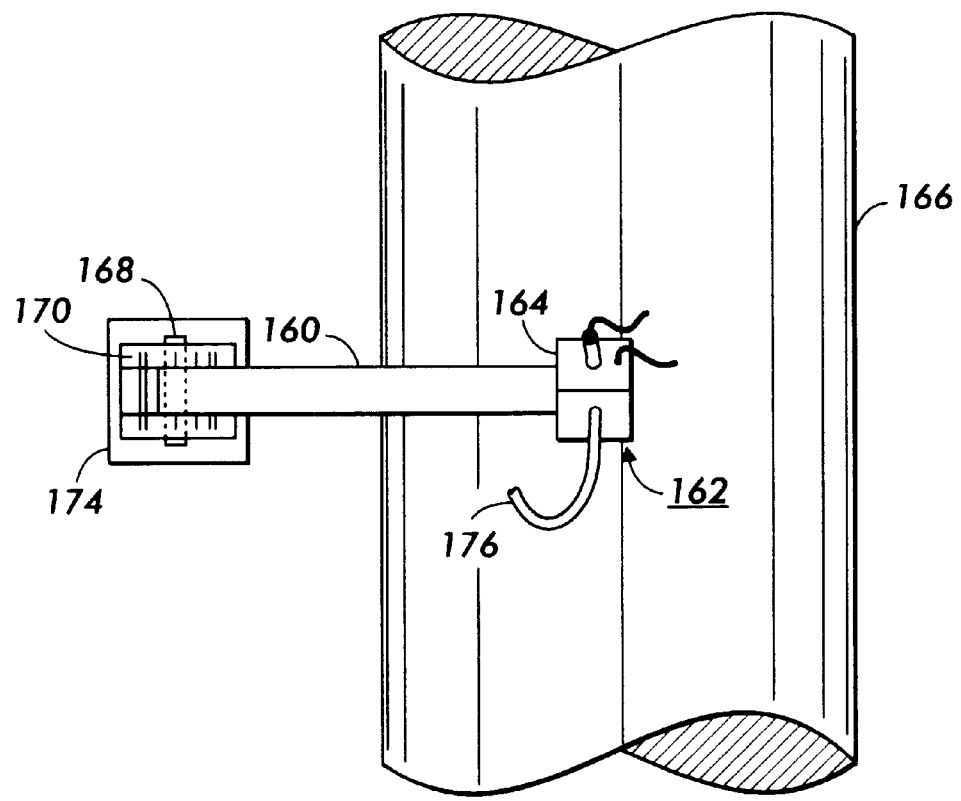
FIG. 13

FIG. 14
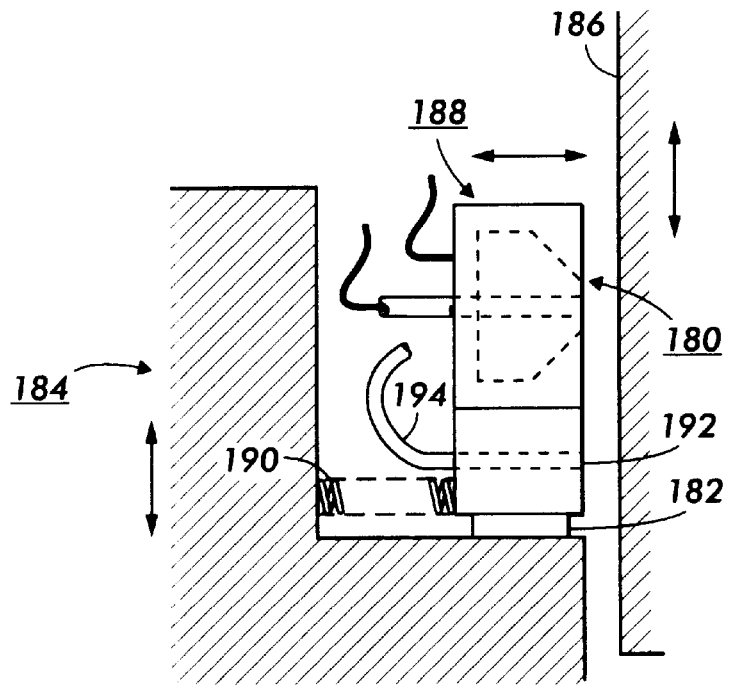
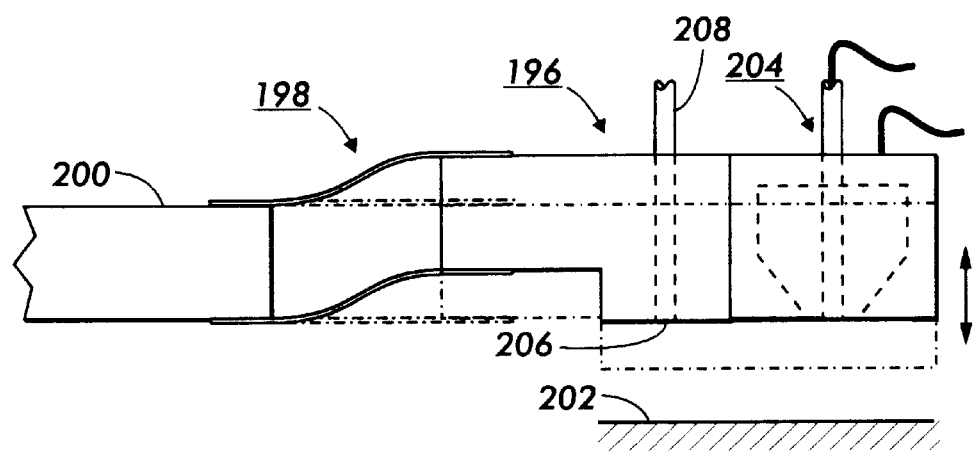
FIG. 15

CONSTANT DISTANCE CONTACTLESS DEVICE

BACKGROUND OF THE INVENTION

This invention relates in general to a scanning system and, more specifically, to a constant distance contactless device and process for using the device.

Although the concept of this invention is intended to include any type of constant distance contactless device for diverse fields such as charge sensing probes for xerography, print heads for ink jet printing, ion stream heads for ionography, extrusion dies for coating, LED image exposure bars, and the like, the following discussion will concentrate on electrostatography for illustrative purposes.

Electrostatography is well known and includes, for example electrography and electrophotography. In electrography, an electrostatic latent image is formed on a nonelectrophotographic imaging member by various means such as styli, shaped electrodes, ion streams and the like. This electrostatic latent image may then be developed to form a visible image by depositing finely divided electroscopic marking particles on the imaging surface.

In the art of xerography, a xerographic plate or photoreceptor comprising a photoconductive insulating layer is imaged by first uniformly depositing an electrostatic charge on the imaging surface of the xerographic plate and then exposing the plate to a pattern of activating electromagnetic radiation such as light which selectively dissipates the charge in the illuminated areas of the plate while leaving behind an electrostatic latent image in the non-illuminated areas. This electrostatic latent image may then be developed to form a visible image by depositing finely divided electroscopic marking particles on the imaging surface.

A photoconductive layer for use in xerography may be a homogeneous layer of a single material such as vitreous selenium or it may be a composite layer containing a photoconductor and another material. One type of composite photoconductive layer used in electrophotography is illustrated in U.S. Pat. No. 4,265,990, the entire disclosure thereof being incorporated herein by reference. A photosensitive member is described in this patent having at least two electrically operative layers. One layer comprises a photoconductive layer which is capable of photogenerating holes and injecting the photogenerated holes into a contiguous charge transport layer. Generally, where the two electrically operative layers are positioned on an electrically conductive layer with the photoconductive layer sandwiched between a contiguous charge transport layer and the conductive layer, the outer surface of the charge transport layer is normally charged with a uniform electrostatic charge and the conductive layer is utilized as an electrode. In flexible electrophotographic imaging members, the electrode is normally a thin conductive coating supported on a thermoplastic resin web. Obviously, the conductive layer may also function as an electrode when the charge transport layer is sandwiched between the conductive layer and a photoconductive layer which is capable of photogenerating electrons and injecting the photogenerated electrons into the charge transport layer. The charge transport layer in this embodiment, of course, must be capable of supporting the injection of photogenerated electrons from the photoconductive layer and transporting the electrons through the charge transport layer.

The photoreceptors are usually multilayered and comprise a substrate, an optional conductive layer (if the substrate is not itself conductive), an optional hole blocking layer, an optional adhesive layer, a charge generating layer, and a charge transport layer and, in some belt embodiments, an anti-curl backing layer.

Although excellent toner images may be obtained with multilayered photoreceptors, it has been found that as more advanced, higher speed electrophotographic copiers, duplicators and printers were developed, reduced life would occasionally be encountered during extended cycling. Surprisingly, cycling of photoreceptors made up of identical materials but differing in overall size and use in different copiers, duplicators and printers exhibited different life spans where one of the causes of failure was dark decay. Moreover, photoreceptors from different production runs had different life spans when cycled to the point of dark decay failure in any given copier, duplicator and printer. Since photoreceptor properties can vary from one production run to another and also during cycling, copy quality in many machines is maintained by feedback control system which constantly adjusts the machine operating parameters to compensate for the variations in the dark decay electrical characteristic of any given photoreceptor. Thus, photoreceptor life is partially governed by the design of the control system and this leads to different life spans in different machines for the same photoreceptor where failure is due to unacceptable dark decay. However, even the control system of any given machine cannot compensate for variations in photoreceptor dark decay characteristics that extend outside the operating range of the control system.

In the production of electrophotographic imaging members the complex nature of the manufacturing process renders unpredictable electrical characteristics of the coated photoreceptor from batch to batch and from month to month. For example, reduction of photoreceptor life due to changes in environment affects the installation or adjustment of new coating applicators or the initial use of a newly prepared batch of coating material for one of the many layers of the photoreceptors such as the hole blocking layer, charge generating layer, or charge transport layer are difficult to identify within a reasonable length of time subsequent to the point in time that the photoreceptor comes off the production line.

In a photoreceptor, many types of microdefects can be a source of xerographic image degradation. These microdefects can be occlusions of particles, bubbles in the coating layers, microscopic areas in a photoreceptor without charge generator layer, coating thickness nonuniformities, dark decay nonuniformities, light sensitivity nonuniformities, and charge deficient spots (CDS's). This last type of defect, charge deficient spots, or CDS's are localized areas of discharge without activation by light. They can cause two types of image defects, depending on the development method utilized. Charge deficient spots usually can be detected only electrically or by xerographic development and so far have eluded microscopic or chemical detection.

In discharged area development, the photoreceptor is negatively charged. An electrostatic latent image, as a charge distribution, is formed on the photoreceptor by selectively discharging certain areas. Toner attracted to discharged areas develops this latent image. Laser printers usually work on this principle. When charge deficient spots are present on the photoreceptor, examination of the final image after toner transfer from the photoreceptor to a receiving member such as paper reveals dark spots on a white background due to the absence of negative charge in the charge deficient spots.

In charged area development, usually used in light lens xerography, the toner image is formed by developing the charged areas on a photoreceptor. After transfer of the toner image to a receiving member such as paper, the charge deficient spot on the photoreceptor will result in a small white spot in a black background called a microwhite, which is not as noticeable as a "microblack" spot, characteristic of discharged area development.

One technique for detecting charge deficient spots in photoreceptors from a specific production run is to actually cycle the photoreceptor in the specific type of copier, duplicator and printer machine for which the photoreceptor was fabricated. Generally, it has been found that actual machine testing provides the most accurate way of detecting charge deficient spots in a photoreceptor from a given batch. However, machine testing for detecting charge deficient spots is a very laborious and time consuming process which requires involving hand feeding of sheets by test personnel along with constant monitoring of the final quality of every sheet. Moreover, accuracy of the test results depends a great deal upon interpretations and behavior of the personnel that are feeding and evaluating the sheets. Further, since machine characteristics vary from machine to machine for any given model or type, reliability of the final test results for any given machine model must factor in any peculiar quirks of that specific machine versus the characteristics of other machines of the same model or type. Because of machine complexity and variations from machine to machine, the data from a test in a single machine is not sufficiently credible to justify the scrapping of an entire production batch of photoreceptor material. Thus, tests are normally conducted in three or more machines. Since a given photoreceptor may be used in different kinds of machines such as copiers, duplicator and printers under markedly different operating conditions, the charge deficient spots detection based on the machine tests of a representative test photoreceptor sample is specific to the actual machine in which photoreceptors from the tested batch will eventually be utilized. Thus, photoreceptor tests on one machine will not necessarily predict whether the appearance of charge deficient spots will occur if the same type of photoreceptor were used in another different type of machine. Thus, for a machine charge deficient spot test, the test would have to be conducted on each different type of machine. This becomes extremely expensive and time consuming. Moreover, because of the length of time required for machine testing, the inventory of stockpiled photoreceptors waiting approval based on life testing of machines can reach unacceptably high levels. For example, a batch may consist of many rolls, with each roll yielding thousands of belts. Still further delays are experienced subsequent to satisfactory charge deficient spot testing because the webs must thereafter be formed into belts, packaged and shipped.

Another test method utilizes a stylus scanner such as that described by Z. D. Popovic et al., "Characterization of microscopic Electrical Defects in Xerographic Photoreceptors", *Journal of Imaging Technology*, vol. 17, No. 2, April/May, 1991, pp. 71–75. The stylus scanner applies a bias voltage to a shielded probe, which is immersed in silicone oil and is in contact with the photoreceptor surface. The silicone oil prevents electrical arcing and breakdown. Current flowing through the probe contains information about defects, and scanning speeds up to 6×6 mm$^2$ in about 15 minutes were achieved. Although the stylus scanner is a highly reproducible tool which enabled some important discoveries about the nature of charge deficient spots, it has the basic shortcoming of low speed.

Many attempts have also been made in the past to reduce the time of scan by designing contactless probes. For example, a probe has been described in the literature and used for readout of xeroradiographic (X-ray) amorphous selenium plates, e.g. W. Hillen, St. Rupp, U. Schieble, T. Zaengel, Proc. SPIE, Vol. 1090, Medical Imaging Ill, Image Formation, 296 (1989); W. Hillen, U. Schieble, T. Zaengel;. Proc. SPIE, Vol. 914, Medical Imaging II, 253 (1988); U. Schieble, W. Hillen, T. Zaengel;. Proc. SPIE, Vol. 914, Medical Imaging II, 253 (1988); U. Schieble, T. Zaemge;. Proc. SPIE, Vol. 626, Medicine XIV/PACS IV, 86 (1986); These probes rely on reducing the distance of a probe to a photoreceptor surface in order to increase resolution of the measurements. The typical distance of the probe to the photoreceptor surface is 50–150 micrometers. In order to avoid air breakdown the ground plane of a xeroradiographic plate is biased appropriately to provide approximately zero voltage difference between the probe and photoreceptor surface.

Accurate measurements of surface potential fluctuations in photoreceptors with high spatial resolution by a charge sensitive probe in order to detect surface potential variations due to charge deficiency spots (CDS's) requires maintenance of controlled distance between the probe tip and the photoreceptor surface being measured. While this can be accomplished by accurate machining of mechanical components, this solution is very expensive and fundamentally not robust. Relatively small external forces and also temperature fluctuations can cause the misalignment of mechanical elements when tolerances on the order of 10 microns are concerned. Variations in probe to sample distance adversely affects reproducibility of tests. Also expensive active control equipment is needed to minimize variations in probe to sample distance. As described above, other examples of systems which need a constant distance contactless device include, for example, charge sensing probes for xerography, print heads for ink jet printing, ion stream heads for ionography, extrusion dies for coating, LED image exposure bars, and the like.

Thus, there is a need for a system that reduces variations in distance between a contactless device spaced from an adjacent surface during relative movement of the contactless device and adjacent surface. For example, reduction of variations in distance of a probe operating at high scanning speeds without arcing for applications such as electrostatographic member production monitoring.

INFORMATION DISCLOSURE STATEMENT

U.S. Pat. No. 5,175,503 to Mishra et al., issued Dec. 29, 1992—A process for ascertaining the projected imaging cycle life of an electrophotographic imaging member is disclosed including the steps of (a) providing at least one electrophotographic imaging member having a cycling life of a known number of imaging cycles, the imaging member comprising an electrically conductive layer and at least one photoconductive layer, (b) repeatedly subjecting the electrophotographic imaging member to cycles comprising electrostatic charging and light discharging steps, (c) measuring dark decay of the photoconductive layer during cycling until the amount of dark decay reaches a crest value, (d) establishing with the crest value a reference datum for dark decay crest value versus imaging cycles, (e) repeatedly subjecting a virgin electrophotographic imaging member to aforesaid cycles comprising electrostatic charging and light discharging steps until the amount of dark decay reaches a crest value which remains substantially constant during further cycling, and (f) comparing the dark decay crest value of the virgin electrophotographic imaging member with the reference datum to ascertain the projected cycling life of the virgin electrophotographic imaging member.

Z. D. Popovic, D. Parco and P. Iglesias, SPIE Vol. 1253 Hard Copy and Printing Materials, Media and Processes, 175 (1990)—A scanning stylus instrument is described for use in the investigation of the electrical properties of individual microscopic defects in organic photoreceptors. A schematic diagram of the measurement circuitry is shown in FIG. 1 on page 176.

Zoran Popovic, Pablo Iglesias, "Characterization of Microscopic Electrical Non-Uniformities in Xerographic Photoreceptors", Fifth International Congress on Advances and Non-impact Printing Technologies, Nov. 12–17, 1989, San Diego, Calif.—An approach to study electrical nonuniformities in photoreceptors is disclosed in which a shielded stylus is used to scan a photoreceptor while in intimate contact with the photoreceptor surface. The photoreceptor is carried on a computer controller X-Y stage. The ground plane of the photoreceptor is connected to the high voltage power supply through a resistor and high voltage relay. A polished stylus tip is brought into contact with the photoreceptor surface. The stylus tip is immersed in silicon oil to prevent electrical breakdown. The presence of silicon oil insulation is absolutely necessary for reproducible measurements. The stylus shield is grounded and the sensing electrode connected to an electrometer to measure the charge flow as voltage is applied to the sample. The whole system is controlled as Xerox 6065 personal computer.

Zoran Popovic, Dave Parco, Pablo Iglesias, "Nature of Microscopic Electrical Defects in Organic Photoreceptors", Proceedings SPIE-SPSE Electronic Imaging Science and Technology Symposium, Feb. 11–16, 1990, Santa Clara, Calif.—The device described in the paper entitled "Characterization of Microscopic Electrical Non-Uniformities in Xerographic Photoreceptors", above, is used to investigate the electrical properties of individual microscopic electrical defects in organic xerographic photoreceptors. The shape of individual microscopic electrical defects were mapped and their current-voltage characteristics were measured.

R. Gerhard-Multhaupt and W. Perry, J. Phys. E; Sci. Instrum. 16, 421–422 (1983).—A scanning capacitive probe is described for the measurement of surface-charge distributions on an electret foils. The probe is a MOSSET electrometer follower together with a high resolution adapter.

E. J. Yarmchuck and G. E. Keefe, J. Appl. Phys. 66 (11), Dec. 1, 1989.—A technique is disclosed for direct, quantitative measurements of surface charge distributions on photoconductors. The photoconductors are carried on a stepping table from a corona charging station to an exposure station and then to the measurement station. Surface charge distribution is determined by a sequence of point-by-point charge measurements at different locations relative to the exposure. Charge measurements are made with an electrometer.

U.S. Pat. No. 3,898,001 to Hardenbrook et al, issued Aug. 5, 1975.—An electrometer system is disclosed which measures electrostatic charges such as a charge level on a photoconductor surface. The electrometer measures a drop in surface voltage in an absence of light on a photoreceptor which is characterized as dark decay, e.g. see Column 1, lines 27–52. The electrometer can measure the remaining or background voltage on a photoreceptor remaining after exposure. The control of this background voltage is important for proper development and copy quality.

U.S. Pat. No. 4,134,137 to Jacobs et al, issued Jan. 9, 1979.—A single wire microelectrometer imaging system is disclosed which includes a means to measure dark decay. A photoreceptor can be selected to minimize dark decay due to a scanning process requiring a finite length of time. A multiple probe electrometer array is provided which comprises a number of single probe electrometers which increase the electronics and gap maintenance complexity while reducing mechanics, image interlace complexities, and processing time.

CROSS REFERENCE TO COPENDING APPLICATIONS

Copending patent application Ser. No. 08/585,133, filed in the name of S. Mishra on Jan. 11, 1996, and now U.S. Pat. No. 5,703,487.—A process is disclosed for ascertaining the microdefect levels of an electrophotographic imaging member comprising the steps of measuring either the differential increase in charge over and above the capacitive value or measuring reduction in voltage below the capacitive value of a known imaging member and of a virgin imaging member and comparing differential increase in charge over and above the capacitive value or the reduction in voltage below the capacitive value of the known imaging member and of the virgin imaging member.

U.S. Pat. No. 6,008,653, entitled CONTACTLESS SYSTEM FOR DETECTING MICRODEFECTS ON ELECTROSTATOGRAPHIC MEMBERS, filed in the names of Z. Popovic et al. on Oct. 30, 1997, and issued Dec. 28,1999.—A contactless process is disclosed for detecting surface potential charge patterns in an electrophotographic imaging member including at least one photoconductive imaging layer having an imaging surface, providing a scanner including a capacitive probe having an outer shield electrode, maintaining the probe adjacent to and spaced from the imaging surface to form a parallel plate capacitor with a gas between the probe and the imaging surface, providing a probe amplifier optically coupled to the probe, establishing relative movement between the probe and the imaging surface, maintaining a substantially constant distance between the probe and the imaging surface, applying a constant voltage charge to the imaging surface prior to relative movement of the probe and the imaging surface past each other, synchronously biasing the probe to within about ±300 volts of the average surface potential of the imaging surface, measuring variations in surface potential with the probe, compensating the surface potential variations for variations in distance between the probe and the imaging surface, and comparing the compensated voltage values to a baseline voltage value to detect charge patterns in the electrophotographic imaging member. This process may be conducted with a contactless scanning system comprising a high resolution capacitive probe, a low spatial resolution electrostatic voltmeter coupled to a bias voltage amplifier, and an imaging member having an imaging surface capacitively coupled to and spaced from the probe and the voltmeter, the probe comprising an inner electrode surrounded by and insulated from a coaxial outer Faraday shield electrode, the inner electrode connected to an opto-coupled amplifier, and the Faraday shield connected to the bias voltage amplifier.

Copending patent application Ser. No. 08/961,061, entitled CONTACTLESS SYSTEM FOR DETECTING SURFACE POTENTIAL CHARGE PATTERNS, filed in the names of S. Mishra et al. on Oct. 30, 1997.—A contactless process is disclosed for detecting electrical patterns on the outer surface of a member comprising providing a member having a charge pattern on an outer surface, repetitively measuring the charge pattern on the outer surface of the member with an electrostatic voltmeter probe maintained at a substantially constant distance from the surface, the distance between the probe and the imaging member being slightly greater than the minimum distance at which Paschen breakdown will occur to form a parallel plate capacitor with a gas between the probe and the surface, the frequency of repetition being selected to cause all time dependent signals to fall out of phase by a predetermined amount, and averaging the out of phase time dependent signals over a sufficient number of measuring repetitions to eliminate the time dependent signals.

The entire disclosures of these three copending applications are incorporated herein by reference.

BRIEF SUMMARY OF THE INVENTION

It is, therefore, an object of the present invention to provide improved processes and apparatus using an aerodynamically floatable constant distance contactless device which overcomes the above-noted deficiencies.

It is another object of the present invention to provide improved processes and apparatus for using an aerodynamically floatable constant distance contactless charge sensitive probe.

It is still another object of the present invention to provide improved processes and apparatus for reducing variations in contactless device to spaced surface distance compared to a contactless device maintained at a fixed distance.

It is another object of the present invention to provide improved processes and apparatus for assessing charge deficient spots in electrostatographic imaging members with excellent reproducibility.

It is yet another object of the present invention to provide improved processes and apparatus for reproducibly positioning a contactless device It is still another object of the present invention to provide improved processes and apparatus for positioning a device which responds to feature changes on an adjacent surface.

It is another object of the present invention to provide improved processes and apparatus for more accurately assessing charge deficient spots in electrostatographic to be employed in discharged area development systems It is yet another object of the present invention to provide improved processes and apparatus for determining charge deficient spots in electrostatographic imaging members to be employed in charged area development systems It is another object of the present invention to provide improved processes and apparatus for assessing charge deficient spots in electrostatographic imaging members without contacting the imaging surface of the imaging member.

It is still another object of the present invention to provide improved processes and apparatus for determining charge deficient spots in electrostatographic imaging members which does not need expensive active control or feedback equipment.

The foregoing objects and others are accomplished in accordance with this invention by providing a contactless system comprising an aerodynamically floatable device, a member having an outer surface adjacent to and spaced from the aerodynamically floatable device, a support mechanism adapted to support the aerodynamically floatable device for free movement toward and away from the outer surface of the member, the aerodynamically floatable device having a side adjacent to, spaced from, parallel to and facing the outer surface of the member, the aerodynamically floatable device also containing at least one passageway for directing at least one stream of a flowing gas from the side of the aerodynamically floatable device toward the outer surface of the member with sufficient pressure to maintain the aerodynamically floatable device a constant equilibrium distance from the outer surface of the member. This system may be utilized in a process comprising providing an aerodynamically floatable device spaced from an outer surface of a member, the aerodynamically floatable device being at least moveable toward and away from the outer surface of the member, the aerodynamically floatable device comprising at least one passageway for directing at least one stream of a gas from the moveable device toward the outer surface of the member, flowing a gas through the passageway with sufficient pressure to maintain the aerodynamically floatable device a constant equilibrium distance from the outer surface of the member.

This system is particularly suitable for processes for detecting surface potential charge patterns in an electrophotographic imaging member comprising providing at least one photoconductive imaging layer having a first major surface on one side and a second major surface on the opposite side, the second major surface comprising an imaging surface, providing a scanner comprising a capacitive probe having an outer shield electrode, maintaining the probe adjacent to and spaced from the imaging surface at a substantially constant distance to form a parallel plate capacitor by flowing pressurized gas from the probe toward the imaging surface, providing a probe amplifier coupled to the probe, establishing relative movement between the probe and the imaging surface, applying a voltage charge to the imaging surface prior to relative movement of the probe and the imaging surface past each other, synchronously biasing the probe to the average surface potential of the imaging surface, measuring variations in surface potential with the probe, and comparing the surface potential values to a baseline voltage value to detect charge patterns in the electrophotographic imaging member.

BRIEF DESCRIPTION OF THE DRAWINGS

A more complete understanding of the present invention can be obtained by reference to the accompanying drawings wherein:

FIG. 12 is a simplified schematic sectional side view in elevation of an aerodynamically floating device embodiment including a probe spaced from a member.

FIG. 13 is a simplified schematic sectional plan view in of the aerodynamically floating device shown in FIG. 12.

FIG. 14 is a simplified schematic sectional side view in elevation of another aerodynamically floating device embodiment which is spring biased toward and spaced from a vertically aligned flat surface of a member.

FIG. 15 is a simplified schematic sectional side view in elevation of another aerodynamically floating device embodiment which is spring biased by double cantilevered springs toward and spaced from a surface of a member.

These figures merely schematically illustrate the invention and are not intended to indicate relative size and dimensions of the device or components thereof.

DETAILED DESCRIPTION OF THE DRAWINGS

Figure 1:
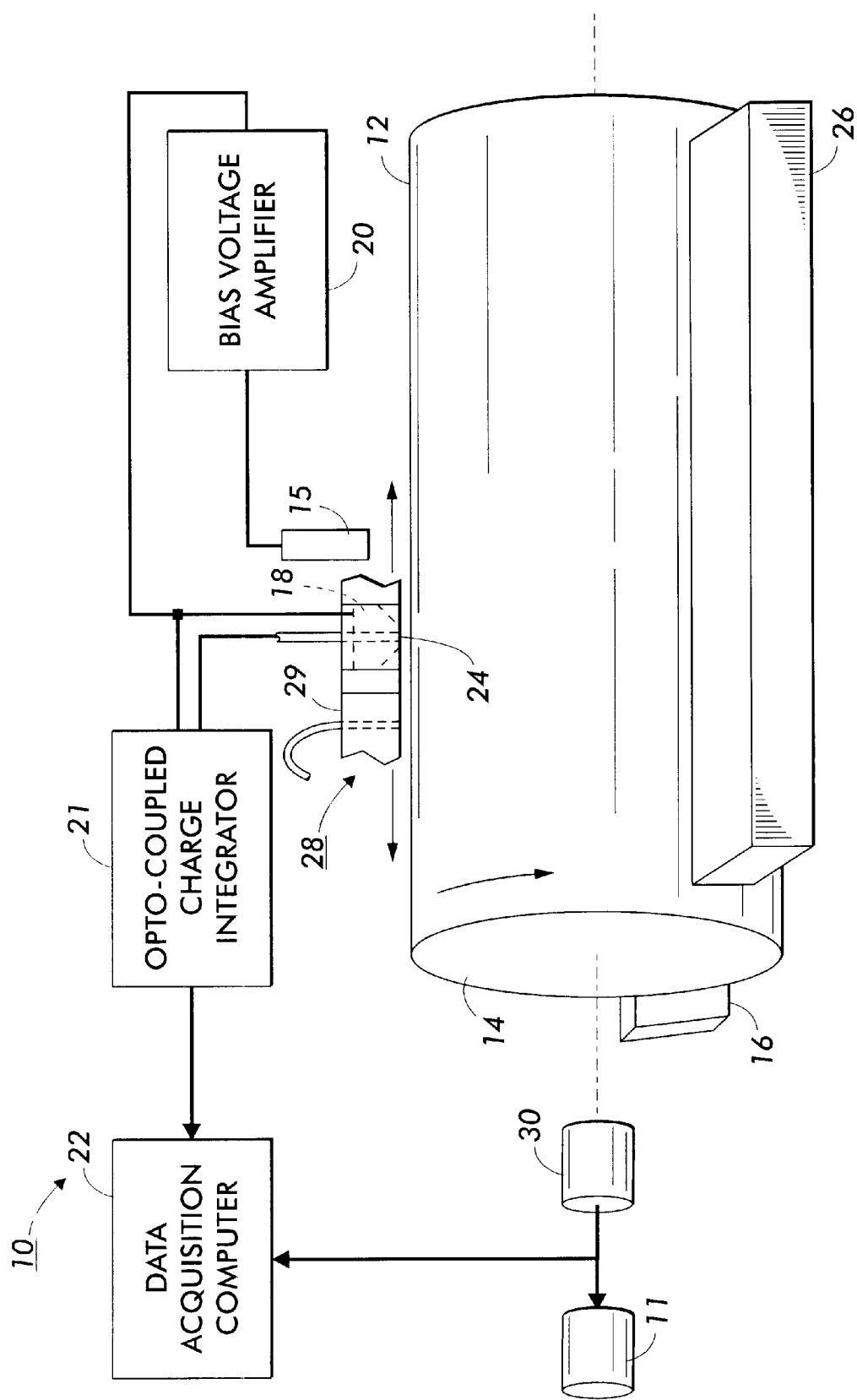
FIG. 1 is a schematic illustration of an embodiment of an optically coupled scanner system utilizing an aerodynamically floating device.

Referring to FIG. 1, a schematic of a scanner system 10 of is shown. Drum is rotated at constant speed by a stepper motor 11. Similar to a xerographic imaging system, a flexible photoreceptor belt 12 mounted on an electrically conductive grounded rotatable drum 14 is charged with a scorotron 16, which electrostatically charges the photoreceptor belt 12 to a constant voltage. Alternatively, the drum 14 may be a photoreceptor drum substrate coated with at least one electrophotographic coating 12. A low resolution electrostatic voltmeter probe 15 and bias voltage amplifier 20 maintain approximately a zero voltage difference between a high resolution capacitive probe 18 and average surface potential of photoreceptor belt 12. The high resolution probe 18, opto-coupled charge integrator 21 and data acquisition computer 22 measure changes in the potential of the moving photoreceptor belt 12 after charging. The lower end 24 of probe 18 has a smooth surface which is parallel to and typically positioned about 100 $\mu$m above the outer imaging surface of belt 12. Time consumed for a section of photoreceptor belt 12 just charged by scorotron 16 to reach probe 18 allows charge deficient spots to form before the spots are scanned by probe 18. Charge on belt 12 is removed with erase light 26 after photoreceptor belt 12 passes probe 18. A stepper motor, micrometer screw and linear bearing combination 28 function as a support mechanism which moves aerodynamically floating device 29 and probe 18 to a new scan line position and the process is repeated. Measurements are started for each scan line by a pulse from encoder 30 at a constant angular position. The "direction of scan" or "scanning direction", as employed herein is defined as the direction of relative movement of the probe over the imaging surface of the photoreceptor belt or drum during the period when probe readings are taken, e.g., in the embodiment shown in FIG. 1, the "scanning direction" would be along a circular path around the circumference of the drum because the drum is rotating past a stationary probe during data acquisition.

The combination of the lower end 24 of probe 18 and the outer imaging surface of photoreceptor belt 12 form a small parallel plate capacitor. It is through this capacitance that a charge deficient spot is detected. Without insulation, the center electrode 36 (see FIG. 2) of probe 18 has a circular cross section with a typical diameter of 113 $\mu$m. At a typical distance of 100 $\mu$m between probe end 24 (which includes the end of center electrode 36) and the outer imaging surface of photoreceptor belt 12, the capacitance is found to be approximately 1 fF, using the approximate relation:

$$C = \frac{A\varepsilon_0}{d} \qquad \text{(Equation 1)}$$

The voltage across this capacitance will be 100 V if 0.1 pC (Q=CV) of charge is present on the probe end 24. Since the surface potential can be determined by using the capacitance-voltage relation, Q=CV, as:

$$V_{surface} = \frac{Qd_{probe}}{A\varepsilon_0} \qquad \text{(Equation 2)}$$

Because V is directly proportional to the probe-sample distance, $d_{probe}$, it is essential that this value be kept constant during scanning to obtain meaningful results. This is complicated by the fact that the drum 14 on which the photoreceptor 12 is mounted is slightly eccentric, with eccentricity of approximately ±25 $\mu$m. Maintaining $d_{probe}$ at an average value of 100 $\mu$m, these variations introduce positioning errors of up to 25 percent. These errors could be reduced with accurate machining of the mounting drum and drum bearings or by employing an active distance control system. Both of these solutions are costly. It is therefore highly desirable to develop a robust and simple method of accurately controlling the probe distance from the photoreceptor surface.

Figure 2:
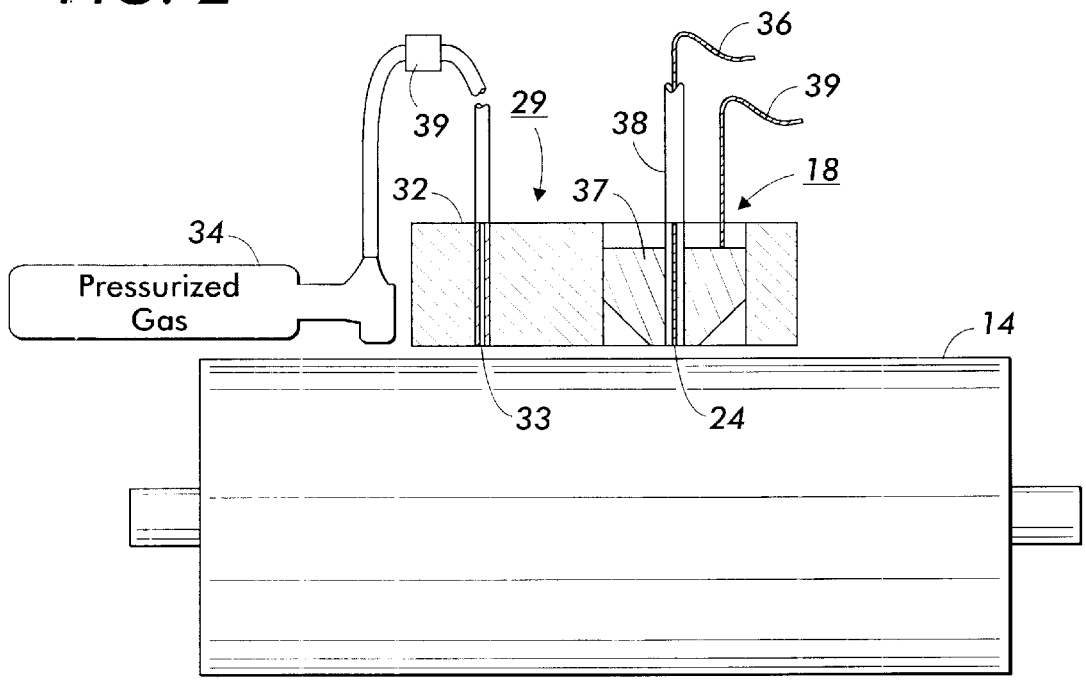
FIG. 2 is a simplified schematic sectional front view in elevation of an aerodynamically floating device spaced from a cylindrical member such as a photoreceptor drum or a photoreceptor belt supported on a cylinder.
Figure 3:
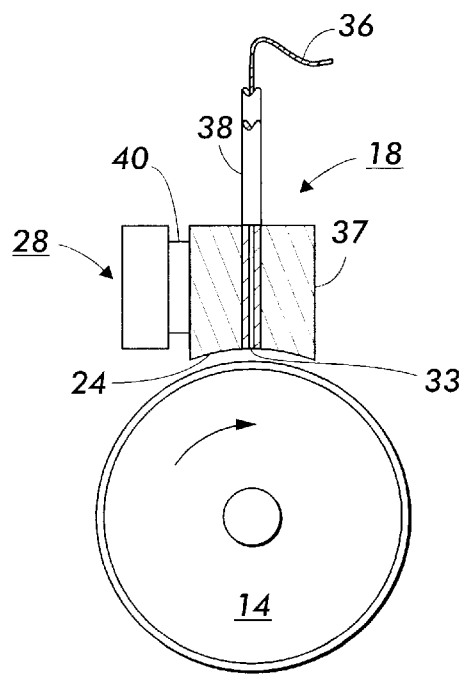
FIG. 3 is a simplified schematic sectional side view in elevation of an aerodynamically floating device spaced from a cylindrical member such as a photoreceptor drum or a photoreceptor belt supported on a cylinder.

Shown in FIGS. 2 and 3, is a greatly enlarged view of the aerodynamically floating movable device 29 which, for the sake of illustrating details, is magnified relative to rotatable drum 14. Aerodynamically floating device 29 comprises flange 32 having a passageway 33 connected at one end through a flexible feed line to a source of compressed gas such as supply tank 34 and open at the other end to direct a stream of gas into the gap between the bottom of movable device 29 and the adjacent surface of drum 14. Supported by flange 32 is probe 18 comprising a small diameter wire center electrode 36 and a conductive shield electrode 37, center electrode 36 and shield electrode 37 being separated by a thin layer of electrically insulating material 38 having a resistivity in excess of about $10^{13}$ ohm cm. Generally, the distance between shield electrode 37 and the outer surface of center electrode 36 is between about 5 and about 50 micrometers. Center electrode 36 is shielded from external noise by shield electrode 37. Changes in potential are sensed through the center electrode 36. The pressurized gas supplied to passageway 33 from supply tank 34 may be regulated by any suitable means such as a pressure regulator valve 39. Typical gas pressure is between about 7 psi and 70 psi or about 0.5 kg/cm$^2$ and 5 kg/cm$^2$. Passageway 33 extends through flange 32 toward the surface of drum 14 to direct a stream of pressurized gas in a direction substantially perpendicular to an imaginary tangent to the surface of drum 14. Motion of flange 32 and probe 35 are restricted by linear bearing 40 (see FIG. 3) to free movement in a direction substantially normal to an imaginary tangent to the surface of drum 14. If desired, any, other suitable device may be substituted for linear bearing 40 such as, for example, linear slide, double cantilevered springs, cantilevered pivot arm (similar to a tone arm on a phonograph player and the like). The lower surface of the flange 32 and the lower end 24 of probe 18 facing the mounting drum 14 is preferably machined and polished to conform to the surface of the drum using emery cloth and diamond paste. Generally, the lower surface of flange 32 is parallel to the outer surface of the adjacent spaced surface such as drum 14. If the aerodynamically floating movable device 29 is to be spaced from a flat surface, the bottom of flange 32, i.e. the surface from which the gas is ejected should be flat and parallel to the spaced flat surface. Shield electrode 37 may be grounded by any suitable means such as a ground wire 39. The edges of probe 18 may be slightly rounded to remove any sharp edges. Excessive electric fields are thus prevented and, if probe 18 happens to come into contact with photoreceptor 12, scratches will be minimized. The lower end of center electrode 36 and bottom of shield electrode 37 may be polished to ensure that they are at the same plane to achieve good shielding and detection properties. If center electrode 36 is recessed too far into shield electrode 37, more electric flux will go into the shield electrode 37 rather than onto the center electrode 36 thereby reducing the signal. If the lower end of center electrode 36 extends beyond shield electrode 37, it could scratch photoreceptor 12. Thus, it is preferred that the lower end of center electrode 36 and the lower end of shield electrode 37 be substantially flush with each other.

The equilibrium distance between aerodynamically floating device 29 and the imaging surface of photoreceptor 12 supported by drum 14 is only weakly dependent on operating parameters. Operating parameters include, for example, probe mass, applied gas pressure and the thermophysical properties of the pressurized gas. The ability of the aerodynamically floating device to respond to variations in the surface features of both a static and dynamic photoreceptor sample is also important.

Equation 1 above gives:

$$C_{coupling} = \frac{A\varepsilon_0}{d_{probe}} \quad \text{(Equation 3)}$$

Inverting this equation gives the calibration curve:

$$\frac{1}{C_{coupling}} = \frac{1}{A\varepsilon_0} d_{probe} \quad \text{(Equation 4)}$$

This equation shows a linear relationship between $1/C_{coupling}$ and $d_{probe}$. Calibration data was obtained by using a capacitance bridge to measure the capacitance between the probe and photoreceptor sample for many value of $d_{probe}$. This method introduced some difficulties, however, because it was not possible to make measurements for extremely small values of $d_{probe}$. To compensate, an arbitrary point close to the surface of the photoreceptor sample 12 was defined to be at $d_{probe}=0$ and all other distances are calculated relative to this artificial benchmark. This has the effect of introducing a constant offset to all distances and applies the mapping $d_{probe} \rightarrow d_{probe}+\delta$ to the equation of the calibration curve. The equation for the calibration equation becomes $$\frac{1}{C_{coupling}} = \frac{1}{A\varepsilon_0} d_{probe} + \frac{1}{A\varepsilon_0} \delta \quad \text{(Equation 5)}$$

The modified calibration curve has the equation of a straight line with a non-zero intercept. Measuring the slope and intercept of the measured calibration line gives values for $A\varepsilon_0$ and $\delta$. Once the quantity $A\varepsilon_0$ is determined the true distance can be determined using Equation 4. Therefore, the calibration curve provides an easy method of determining separation distance in investigations by measuring the capacitance between the probe 18 and photoreceptor sample 12.

An important operating parameter of the aerodynamic floating system of this invention is the amount of mass which can be supported by the compressed gas. In a specific implementation of the aerodynamic floating mechanism, the mass of the aerodynamically floating movable device 29 combination was approximately 20 grams. To demonstrate how mass affects equilibrium distance of the lower end of probe 18 to the imaging surface of photoreceptor 12, additional masses of up to 40 grams were attached to the flange 32, thereby tripling the mass being supported by aerodynamic floating. Nitrogen gas from a cylinder was used to provide aerodynamic floating for this embodiment. A plot of applied mass vs. equilibrium distance was prepared. A relatively small slope of −0.17 µm/g indicated that equilibrium distance has only a weak linear dependence on the applied mass. A total decrease of only 8 micrometers in gap distance was observed at maximum loading (a 200 percent increase), representing a 14 percent decrease from the original equilibrium distance (no additional load). The extremely weak dependence on applied mass allows for the capability of adding additional equipment to the aerodynamically floating movable device without substantially affecting system performance. Generally, the mass of the aerodynamically floating movable device that can be maintained at a given equilibrium distance depends on the number and size of passages in the device for the flowing compressed gas and the pressure of the flowing compressed gas.

There is an extremely weak dependence on the applied gas pressure. The effects of varying the gas pressure for the aerodynamic floating movable device 29 were investigated using, for example, nitrogen gas at pressures of 15–50 psi (1 atm. −3.5 atm.). The equilibrium position for each level of applied pressure was recorded. This experiment was repeated twice and the results were plotted. A mean equilibrium position of 59 µm with a variation of ±5 mm was recorded. This shows a variation of less than 10 percent in equilibrium distance over a pressure range from 15 psi up to 50 psi, implying an extremely weak dependence on the applied gas pressure. Furthermore, equilibrium distances are extremely reproducible, with an average difference of only 2.5 µm between the two recorded data sets. Agreement between the data sets increased with increasing pressure. Additional experiments using compressed air instead of nitrogen gas showed no difference in either the level or variation of the gap distance.

Figure 4:
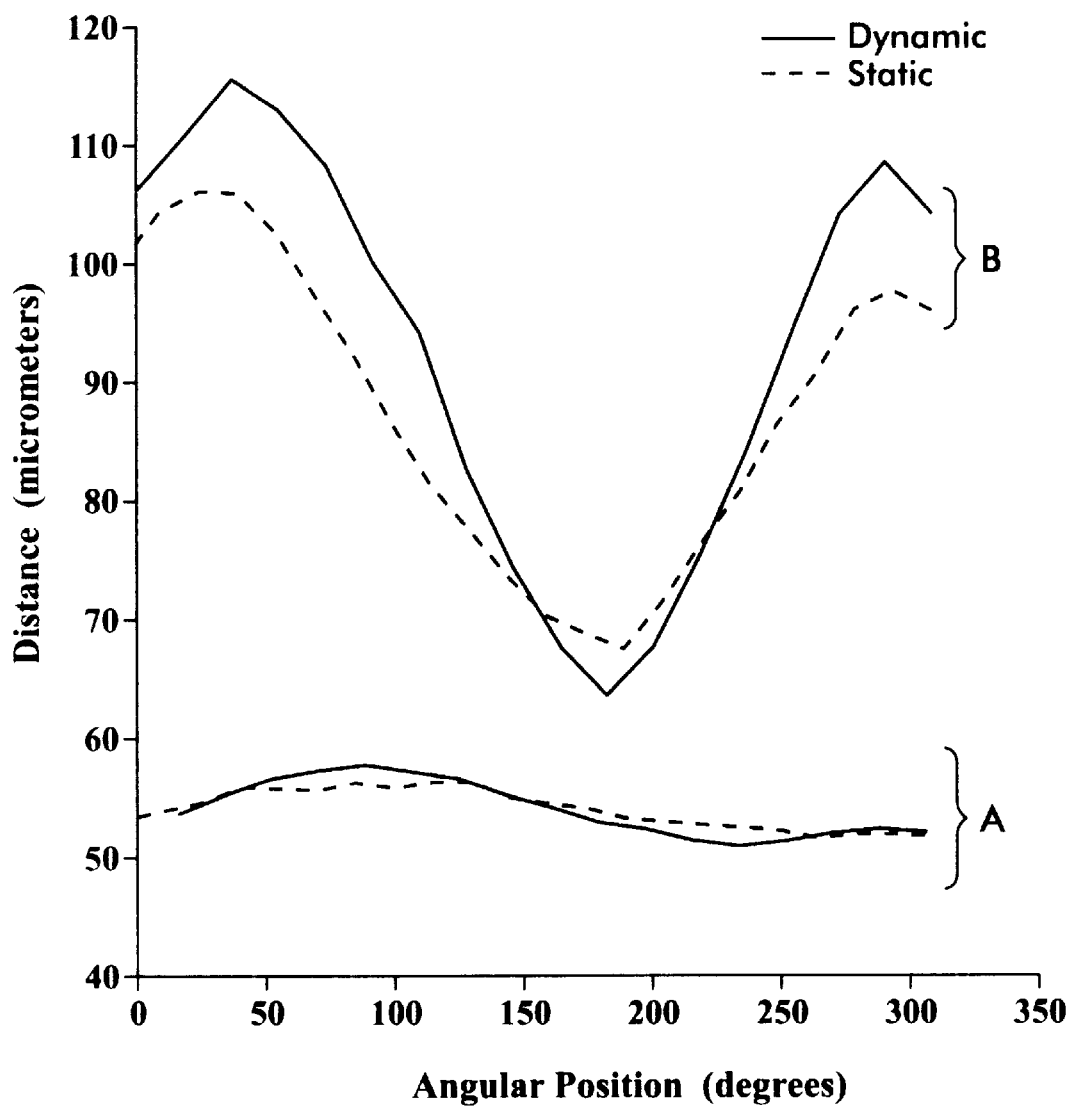
FIG. 4 is a graph of drum to aerodynamically floating device distances for static and dynamic measurements with (A) and without (B) flowing pressurized air. In the case (B) the position of the device is held fixed mechanically.

To be useful as a tool for quality control, it is essential that the aerodynamic floating device be able to maintain a constant probe to photoreceptor sample distance regardless of small eccentricities of the support drum 14. The aerodynamic floating device 32 must also be able to adapt to changing surface features on the photoreceptor sample itself. Two experiments illustrate how well the aerodynamic floating device 29 of this invention adapts to these conditions. In the first, the ability of aerodynamic floating device 29 to adapt to the eccentricity of the mounting drum was examined. The aerodynamic floating device 29 was positioned over the mounting drum 14 with no photoreceptor sample 12 in place, and equilibrium distance between the bottom 24 of probe 18 and the surface of drum 14 was measured. The drum 14 as rotated to a new angular position and new probe to drum distance measurements were taken when the system again came to equilibrium. To compare the relative advantages of aerodynamic floating versus a fixed level probe, probe to drum distances were also measured with a probe held by a stop screw approximately 90 µm above the surface of the drum 14. The results of the experiment are illustrated in FIG. 4. The eccentricity of the drum was readily apparent from the measurements taken without the use of aerodynamic floating. The average equilibrium distances were found to be 54 µm and 93 µm for the measurements taken with aerodynamic floating (see dashed line in A) and without aerodynamic floating (see dashed line in B), respectively. While this data is for illustrating the merits of aerodynamic floating, it was collected with a mounting drum 14 in a static configuration. When the drum 14 was moved to a new angular position to acquire a new measurement, the probe was allowed sufficient time (seconds) to come to a new equilibrium position. To illustrate the performance of the aerodynamic floating system of this invention in a dynamic situation, the drum 14 was set to rotate with a surface speed of 15 inches/sec, as in a typical test operation. The measurements obtained using this method are also illustrated in FIG. 4. As with the data obtained with the drum in a static configuration, the rotating drum showed an average probe to drum distance of approximately 53.6 µm for the aerodynamic floating system of this invention (see solid line in A), which differs by only 0.7 percent from the measurements taken from the static drum. The rotating drum also showed the same distance variations of ±3.5 µm previously observed in the static configuration. Results of a fixed probe without aerodynamic floating is represented by the solid line in B of FIG. 4. The agreement between measurements taken from the mounting drum 14 in static and rotating (dynamic) configurations implies that drum rotation provides no impediment to accurate distance control with the aerodynamic system of this invention.

All of these measurements were made with the probe positioned over an area of bare supporting drum, with no photoreceptor in place. The imaging surface of a photoreceptor 12 is less uniform than the support drum surface and this non-uniformity can potentially present a substantial obstacle to obtaining reproducible positioning for ordinary fixed level probes. To demonstrate that aerodynamic floating can accurately position a probe over a photoreceptor sample, a photoreceptor sample was attached to the mounting drum 14 as it would be during normal scanner operation, and probe 18 was moved to a position over the sample. Because photoreceptors have a different dielectric strength than air, the probe 18 was recalibrated. In the demonstrations described above, only an air gap existed between the probe 18 and the mounting drum 14, allowing the distance to be calculated relatively easily. When a photoreceptor 12 was mounted on the mounting drum 14, the gap between the probe 18 and ground plane of photoreceptor 12 changed to one partially filled with a dielectric. This required correcting the 1/C versus d curve for photoreceptor capacitance. The correction is straightforward and fundamentally involves subtracting the dielectric thickness of the photoreceptor (e.g. 9 µm) from the distance determined using the calibration described above. While the equilibrium position over the photoreceptor 12 is not identical to the equilibrium position over a bare mounting drum 14, the difference was small (about 5 µm), and the variation with position is very similar. The difference in equilibrium distances between photoreceptor 12 and the bare drum 14 may be due to small play of the linear bearing 40 as it is of the same order as the error of 2.5 µm obtained from two successive measurements. Under all conditions, the equilibrium position of the scanner probe 18 shows only minor variations which are substantially smaller than variations measured when using only a fixed level probe. Drum rotation has no significant effect on equilibrium position. While equilibrium distance appeared to change when the probe was positioned over the photoreceptor, the variations in the distance were very small, and comparable to those observed under other operating conditions of the aerodynamic floating system of this invention. In general, the aerodynamic floating system of this invention surprisingly shows a remarkable independence from all important operating parameters.

Any suitable gas may be utilized for the aerodynamic floating system of this invention. The equilibrium position of the aerodynamic floating system was measured using several different gasses to provide aerodynamic floating support. Compressed air, argon, hydrogen, helium and carbon dioxide gases were used. The thermophysical properties of the gas used to provide hydrodynamic support plays an important role in defining the equilibrium distance of the probe. For gas pressures ranging in 10 psi increments from 10 psi to 50 psi, for hydrogen, helium, argon, air and carbon dioxide ($CO_2$ measured at 30 psi only), it was found that the gap size depends only weakly on gas pressure and the average equilibrium gap sizes for these gases were 68.5 µm, 86.89 µm, 50.86 µm, 49.55 µm and 40.63 µm, respectively. There do not appear to be any strong correlation between average equilibrium gap size and the ratio of thermodynamic heat capacities at constant pressure and constant volume, the gas density, the molecular mass of the gas, or the speed of sound for each gas. Thus, the thermophysical properties of the pressurized gas used in the system affect the equilibrium distance measured, but the distance varies only slightly with gas pressure. Molecular mass, viscosity and the speed of sound in the gas do not correlate well with equilibrium position, but there is a strong linear dependence on the square root of the mean free path of the gas. The expression "mean free path of the gas", as employed herein, is defined as a mean distance traveled by a molecule before collision with other molecules. The equilibrium position of the probe 18 bears a linear relationship with the square root of the mean free path of the gas. In other words, the equilibrium distance is directly proportional to mean free path. Thus, it is hypothesized that boundary layers form near the walls which channel the gas flow are responsible for the existence of a stable equilibrium distance. A rough approximation of the equilibrium distance may be obtained with the following formula:

$$d_{equilibrium} = 2 \, (lL)^{1/2}$$

wherein:

$d_{equilibrium}$ is the equilibrium distance,

L is a typical linear dimension of the aerodynamic floating device, l is the mean free path of the molecules in the gas which is available in handbooks (typical mean free paths include hydrogen=11.8 nm, helium=18.6 nm, argon=6.66 nm, air=6.79 nm, carbon dioxide=3.97 nm).

Thus, for the aerodynamic floating probe described above where L=0.5 inch=12.7 millimeters and l (mean free path)

for argon=63.5 nm to give $d_{equilibrium}$=57 μm which is in close agreement with the actual measured value of 51 μm.

As described above with reference to FIG. 3, a typical gap distance of 100 μm between the lower end 24 of probe 18 and a voltage of 100 volts corresponds to 0.1 pC of charge induced into probe 18. Preferably, the gap distance is between about 20 micrometers and about 200 micrometers and more preferably between about 50 micrometers and about 100 micrometers. When the gap is less than about 20 micrometers, there is increased risk of probe touching the surface which can lead to erroneous results. If the gap is greater than about 200 micrometers, the probe sensitivity and resolution are substantially reduced. The lower end 24 of probe 18 and bottom of flange 32 facing the imaging surface of photoreceptor belt 12 supported on drum 14 are machined and polished to conform to the shape imaging surface so that the spaced surfaces are parallel to each other. When gas under pressure, typically between about 1 kg/cm$^2$ and about 5 kg/cm$^2$, is pumped through the conduit 31 it escapes with high velocity into the space between flange 32 and the imaging surface of photoreceptor 12 leading to a pressure drop due to the Bernoulli effect. This pressure drop leads to an attractive force between flange 32 (carrying probe 18 ) and the imaging surface and probe 18 is maintained at a distance of about 50 microns from the imaging surface of photoreceptor 12. The equilibrium distance between probe 18 and the imaging surface weakly depends on the gas pressure. A change of pressure from 1 kg/cm$^2$ to 3.5 kg/cm$^2$ changes the distance by only about 10 percent. Loading of probe 18 by up to 40 gm of weight (a typical weight of probe 18 by itself is about 20 gm) at 2 kg/cm$^2$ applied gas pressure changes the distance again by only about 10 percent. These values are maintained when the imaging surface is moving (the drum is rotating) at a speed of about 15 inch/sec (38.1 cm/sec). During relative motion between probe 18 and the imaging surface there is no mechanical contact between probe 18 and the imaging surface because probe 18 is basically riding with minimum friction on an air cushion formed by the flowing gas.

Any suitable number of passageways may be utilized. The passageway may be straight or curved. However, it is preferred that the outlet of the passageway be aligned to direct the flowing stream of gas toward the spaced surface of the adjacent member. The passageways may comprise a single unrestricted tunnel or a tunnel containing restricting structure such as baffles. The passageways may have any suitable cross sectional shape such as round, octagonal, square, rectangular, triangular, honeycombed, and the like. The cross sectional area of a passageway depends upon the total number of passageways employed, the surface area of the bottom of the aerodynamically floating device, and the mass of the aerodynamically floating device. A typical cross sectional area for a single passageway is between about 1 square millimeter and about 100 square millimeters.

The fact that the force between flange 32 and the surface of photoreceptor 12 is attractive renders the system of this invention quite robust. As illustrated by curves A of FIG. 4, both static without flowing pressurized air (dashed line) and dynamic without flowing pressurized air (solid line) measurements with drum 14 rotating at 15 inch/sec (38.1 cm/sec), give the same distance variations as a function of the angular position of drum 14. Small distance variations (about 8 micrometers total) observed around the drum circumference are perfectly reproducible and probably represent the true distance variation between the positions of the air jet and the charge sensitive capacitive probe. All distances were measured by the capacitance method after the probe capacitance versus distance curve had been established. If aerodynamic floating is not employed and the probe 18 is held at the fixed position above the drum, the distance variations are much larger, amounting to about 50 micrometers, as shown in curves B of FIG. 4 (static with flowing pressurized air represented by dashed line and dynamic with flowing pressurized air represented by solid line). These variations are determined by the accuracy of machining and concentricity of the drum surface and the axis of rotation.

Figure 5:
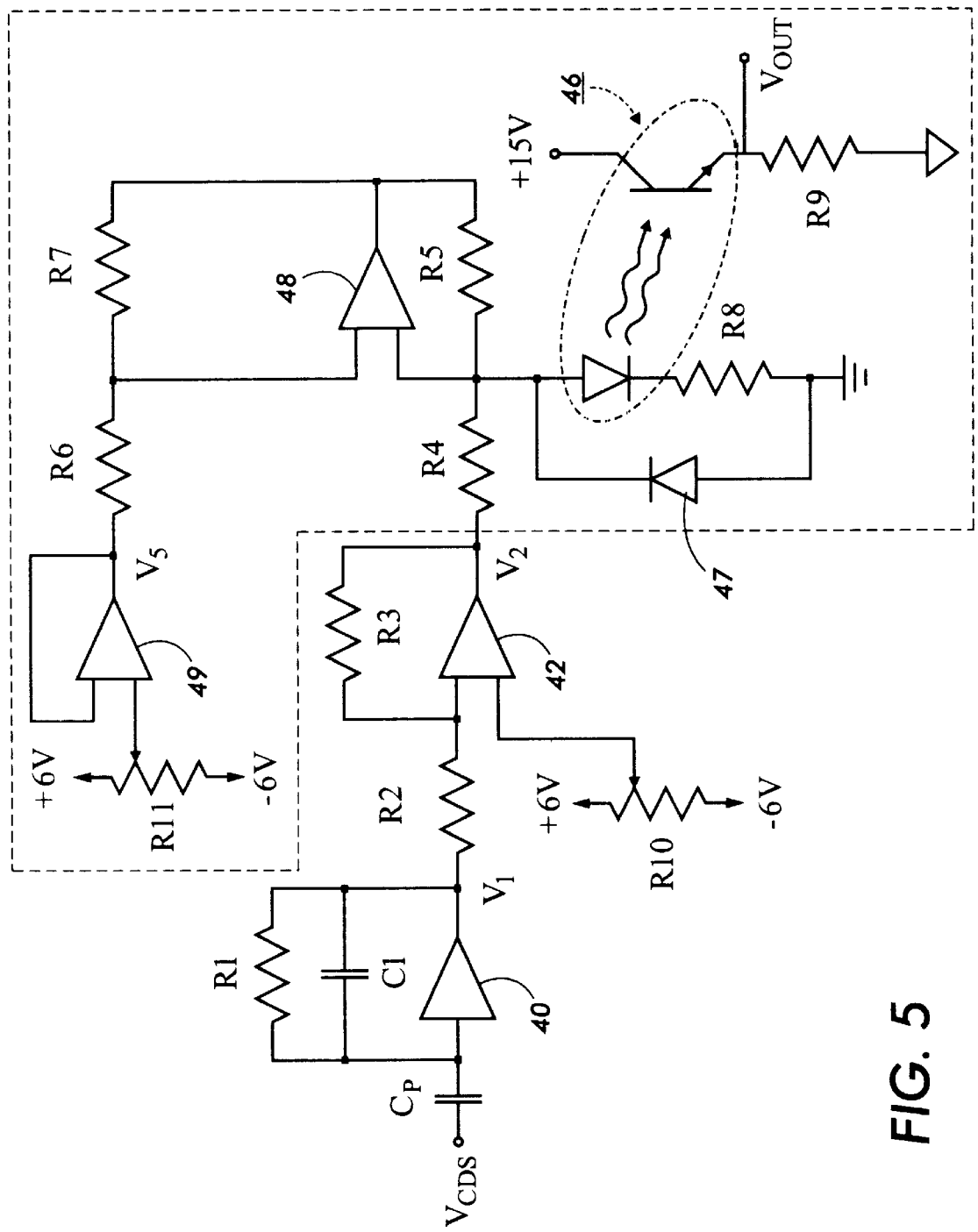
FIG. 5 is a circuit for an optically coupled charge integrating amplifier for an optically coupled scanner system that uses an aerodynamically floating probe.

Referring to FIG. 5, an example of a circuit is shown for an optically coupled charge integrating amplifier for the optically coupled scanner system. The optocoupled part of the amplifier is surrounded by the phantom lines. The first stage of the amplifier integrates the signal $V_{CDS}$ from probe 18 and amplifies it. A charge integrating amplifier 40 such as an Amptek A250 operational amplifier with internal $C_1$=7 pF and $R_1$=300 MΩ feedback components was used as the first stage. A buffer amplifier 42 was used as a second stage to further increase the signal level from integrating amplifier 40. With a gain of 20, amplifier 42 amplified the signal to a level appropriate for the data acquisition board. A variable resistor R 10 in the second stage was used to compensate for unwanted offsets. Compensation for offsets from the first stage integrating amplifier 40 was readjusted each time the gain was changed. If the ground of probe 18 and the amplifier circuit is grounded to zero volts, a serious problem arises. When the outer imaging surface of photoreceptor 12 is at 1000 V and the shield electrode 37 is at 0V, dielectric breakdown can occur.

The capacitance between the probe 18 and ground plane of photoreceptor belt 12 is inversely proportional to the distance between the end 24 of probe 18 and the outer imaging surface of photoreceptor belt 12. To continuously measure a distance, a 100 V square wave pulse was applied to the probe 18 synchronously with the data acquisition frequency, in addition to the bias voltage equal to photoreceptor surface potential. The data acquisition system takes readings at the maximum and minimum points of the 100 V wave. Two consecutive readings by the computer 22 will provide a measurement at 0 and 100V points of the wave. The distance between these two values is inversely proportional to the local distance between the end 24 of probe 18 and the outer imaging surface of photoreceptor belt 12. Calibration was accomplished with a series of readings. The distance between the end 24 of probe 18 and ground plane of photoreceptor belt 12 incrementally increased by a predetermined fixed amount after each reading. Taking the inverse of these values and fitting them to a straight line produced a slope which is used for calibration. For a given reading difference, the distance can be calculated using the slope.

A Paschen curve can be used to predict when breakdown between probe 18 and the underlying photoreceptor may occur. Paschen curves are well known in the art and described, for example in R. M. Schaffert, *Electrophotography*, Focal Press Limited, London, 1975. By applying a bias potential to the shield electrode 37 and ground of the probe 18, that is equal to the average potential of the outer imaging surface of the photoreceptor 12, the voltage gradient will be reduced close to zero and prevent breakdown. An electrostatic voltmeter probe 15 e.g. Trek, Model 368 (see FIG. 1), may be used to measure the average surface potential on the outer imaging surface of the photoreceptor 12. The output of voltmeter probe 15 is fed to bias voltage amplifier 20, e.g., Trek 609A (see FIG. 1), which applies the electrical bias to the shield electrode 37 of probe 18. The electrostatic voltmeter probe 15 is a low spatial resolution electrostatic voltmeter which does not sense defects as small as charge deficient spots and thus the bias on shield electrode 37 will not be affected by charge deficient spots. Since arcing can be avoided if the shield electrode 37 is biased to a potential within about ±300 volts of the average surface potential on the outer imaging surface of the photoreceptor 12 and since the average surface potential may be roughly determined by the scorotron voltage minus the potential drop due to dark decay, one may alternatively apply a bias on shield electrode 37 without using an electrostatic voltmeter probe 15 so long as the applied bias is within about ±300 volts of the average surface potential on the outer imaging surface of the photoreceptor 12. Thus, for example, when the voltage to the charging scorotron is 1000 volts and the dark decay of the photoreceptor reduces the photoreceptor surface potential to 800 volts, the bias to be applied to the shield electrode of the probe is preferably between about 500 volts and about 1100 volts, i.e. within about ±300 volts of the average surface potential on the outer imaging surface of the photoreceptor. To isolate the computer data acquisition system from the high voltage probe bias, an optoisolator 46 comprising a light emitting diode and a phototransistor has been utilized. The optoisolator 46 is comprised of light emitting diode and a phototransistor in a single package. A Howland voltage to current converter, comprised of the operational amplifier 48 and resistors $R_4$, $R_5$, $R_6$, and $R_7$, powers the light emitting diode of a 4N35 opto-isolator 46 (see components within phantom lines in FIG. 3). Howland voltage to current converters are known and described, for example, in J. I. Smith, *Modern Operational Circuit Design*, John Wiley & Sons, Inc., New York, 1971, the entire disclosure thereof being incorporated herein by reference. Bias current of the voltage to current converter depends on the voltage at $V_5$, and is adjusted using the operational amplifier 49 and the variable resistor ($R_{11}$). The isolated end of the circuit, comprised of phototransistor part of optoisolator 46 and resistor $R_9$ is an emitter follower amplifier which provides the signal of a charge deficient spot without the high voltage component. Optocoupled amplifiers are well known in the electronic art. Any suitable optocoupled amplifier may be employed in the scanning system of this invention. The connecting of the probe to the optocoupled amplifier allows biasing of the probe itself to the photoreceptor average surface potential rather than biasing of the ground plane of the photoreceptor thereby preventing air breakdown and arcing. The optically coupled amplifier denoted by the phantom lines provides the probe signal which is recorded by the data acquisition computer in the scanner system of this invention. The expression "optically coupled" or "optocoupled" as employed herein is defined as providing transmission of an electrical signal without an electrical connection by using an electrically driven light source and a light detector which is insulated from the light source. A key result from using an optically coupled amplifier is that the probe is electrically isolated from the amplifier output and can, therefore, be biased to any potential. Thus, the average surface potential of the surface of photoreceptor 12 is measured with a standard electrostatic voltmeter 15 and the shield electrode 37 of scanner probe 18 is biased to the same potential. In this way the possibility of arcing between the probe end and photoreceptor surface is eliminated and a factor which would greatly impact results of the measurements is overcome. Previously the ground plane of the photoreceptor was biased so that the potential between the probe and photoreceptor surface was zero or very small.

This is practical for drums and laboratory experiments but impractical for large belts, in particular for testing rolls of belts in a production environment. The amplifier for probe 15 is an AC coupled amplifier. Therefore only variations of the potential can be measured on the time scale determined by the time constant of the amplifier. This time constant is typically about 2 milliseconds but can be larger or smaller or the amplifier could even be a DC coupled amplifier. In this way only fluctuations in the surface potential are measured with spatial frequency determined by the photoreceptor surface speed and the time constant of the amplifier. With these characteristics the probe 18 is ideally suited to detect charge deficient spots (CDS's) which are very small areas of a photoreceptor having significantly lower potential than the average photoreceptor potential. Charge deficient spots have a potential of more than about 50 volts and occupy an area of between about 20 micrometers and about 200 micrometers. The aerodynamically floating scanning system of this invention can also be used to detect fluctuations in photoreceptor surface potential induced by any other causes such as coating nonuniformity, nonuniform dark decay, and the like. Thus, the scanner system can serve as an instrument to determine surface potential uniformity on small length scale (less than about 1 millimeter) for which standard electrostatic voltmeter probes are not suitable.

Generally, a probe with center electrode having a round cross section provides higher resolution than a probe with center electrode with a rectangular cross section, the linear dimension of both electrodes being the same in the scanning direction. For center electrodes having a round or circular cross section, satisfactory results may be achieved with a diameter between about 20 micrometers and about 500 micrometers. Preferably, the diameter is between about 100 micrometers and 200 micrometers. When the diameter is less than about 20 micrometers, the signal from the probe may be too small to be accurately detected. If the diameter is greater than about 500 micrometers, the probe resolution becomes similar the spatial resolution of standard electrostatic voltmeter probes. For center electrodes having a rectangular cross section, satisfactory results may be achieved with a width between about 20 micrometers and about 500 micrometers and a length of between about 0.5 millimeter and about 10 millimeters, the length (longest side) being the side of the electrode which is perpendicular to the direction of scan (e.g. the direction of scan in the embodiment shown in FIG. 1 is in a direction perpendicular to the axis of drum 14 and parallel to an imaginary line circumscribing the drum). When the width is less than about 20 micrometers, probe sensitivity decreases significantly. If the width is greater than about 500 micrometers, conventional electrostatic voltmeter probes become more suitable for these measurements. When the length is less than about 0.5 millimeter, there is relatively small increase in the scanning speed of the photoreceptor area. If the length is greater than about 10 millimeters, the probe noise may become a problem.

For a circular 100 $\mu$m diameter probe, photoreceptor drum diameter of 3" (7.62 cm) and rotation speed of 1 revolution per second, a scanned speed of 1 in$^2$/min (6.45 cm$^2$/min) can be achieved with the scanning system. In order to achieve this speed, the data acquisition rate is about 2.5 kHz which is easily accessible by conventional digital data acquisition instrumentation available for any suitable personal computer. For a rectangular 0.2 millimeter×5 millimeter probe center electrode, where the 5 millimeter side was parallel to the axis of the photoreceptor drum, a scanning speed of 13 in$^2$/min (83.85 cm$^2$/min) was achieved. The scanning speeds in experiments conducted were limited by computer speed and time necessary to move the probe parallel to the drum axes. These speeds can be further increased by using probe arrays and faster computers for data processing. This enables on-line inspection for charge deficient spots as photoreceptors are being coated. Scanning speeds can be at least about 1 inch per second and include, for example, scanning of the imaging surface with the probe at a speed of between about 1 inch per second and about 100 inches per second.

Figure 6:
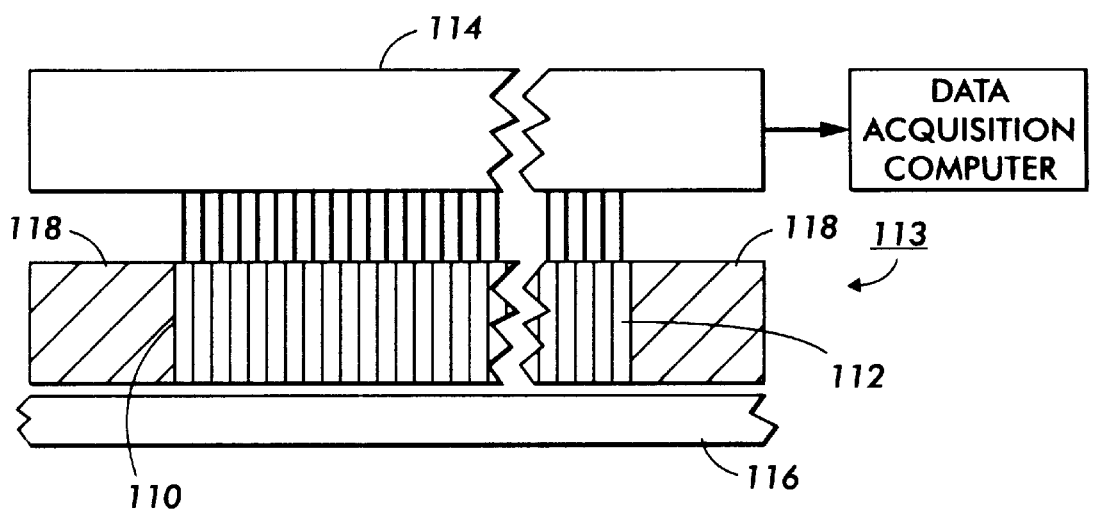
FIG. 6 is an array of probe elements ganged together.

As shown in FIG. 6, multiple scanner probes including first probe electrode element 110 through Nth probe electrode element 112 may be ganged together into an array 113 and operated in a multiplex mode with an N channel optically coupled amplifier 114 outputting to a data acquisition computer. This type of system will increase the rate of scan of the surface of an electrostatographic member 116. Each probe electrode element is electrically insulated from the surrounding shield 118.

Figure 7:
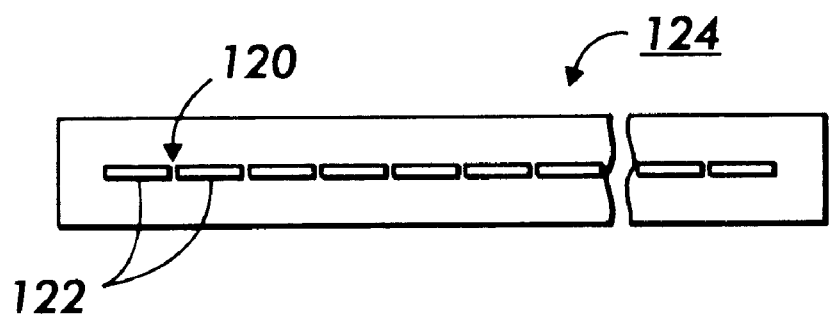
FIG. 7 is an array of probe elements ganged together with small gaps between elements illustrated.
Figure 8:
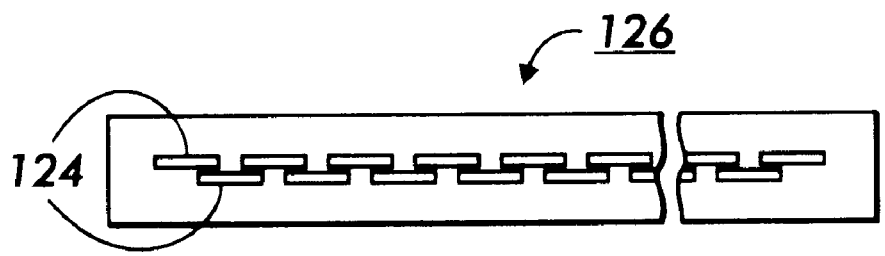
FIG. 8 is an array of probe elements ganged together in staggered rows.

As illustrated in FIG. 7, small gaps 120 may be provided between different electrode elements 122 of a probe array 124. Preferably, but not necessarily, the gap may be smaller than the gap distance between the end of probe array 122 and the adjacent surface of an electrostatographic member. While the probe electrode elements 122 in FIG. 6 are shown aligned in a single row, they may be arranged as staggered probe electrode elements 124 in the array 126 illustrated in FIG. 8. The staggered probe electrode arrangement enables the scanning of the photoreceptor surface without any effects normally encountered due to small gaps between individual probe elements of a single row array.

Figure 9:
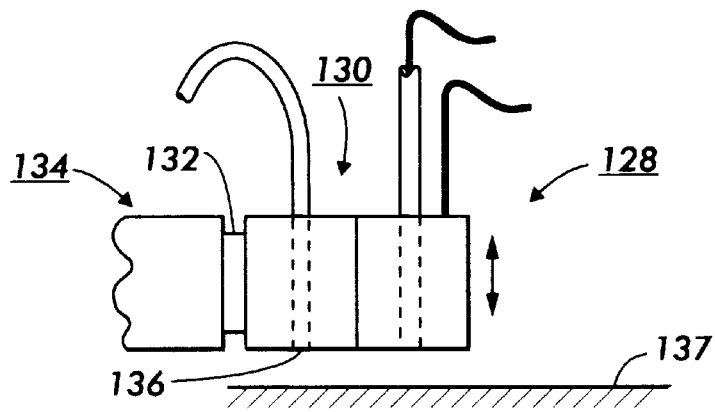
FIG. 9 is a simplified schematic sectional side view in elevation of an aerodynamically floating device embodiment including a probe array spaced from a flat member.
Figure 10:
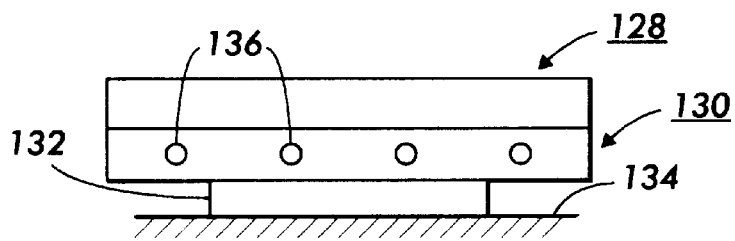
FIG. 10 is a simplified schematic sectional plan view in of the aerodynamically floating device shown in FIG. 9.

As shown in FIGS. 9 and 10, a probe array 128 (which may, for example, be any of the arrays shown in FIGS. 6–8) is supported by an aerodynamically floating flange 130. Aerodynamically floating flange 130 is, in turn, supported by a linear bearing 132 attached to a transport assembly 134 comprising a stepper motor and micrometer screw combination similar to that illustrated in FIG. 3. Aerodynamically floating flange 130 can also be allowed to rotate around a bearing (not shown) whose axis is perpendicular to the plane of the linear bearing thus allowing for the automatic leveling of the probe array 128 whereby the flat bottom surfaces of the array 128 and flange 130 are maintained parallel to the adjacent underlying surface 137. Aerodynamically floating flange 130 may be similar to aerodynamically floating device 29 shown in FIGS. 1 and 2 except for size, relative location and the plurality of gas passageways 136.

Figure 11:
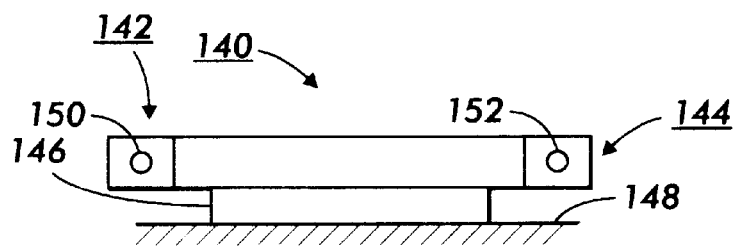
FIG. 11 is a simplified schematic sectional plan view of another embodiment of an aerodynamically floating device in which aerodynamically floating flanges are fastened to opposite ends of a probe array.

Illustrated in FIG. 11 is another embodiment of this invention in which an array 140 is supported at each end by a pair of aerodynamically floating flanges 142 and 144. A linear bearing 146 secures array 140 to a supporting frame 148 for free movement toward or away from an underlying surface (not shown). Aerodynamically floating flanges 142 and 144 contain at least one gas passageway 150 and 152, respectively. Aerodynamically floating flanges 142 and 144 along with array 140 can also be allowed to rotate around a bearing (not shown) having an axis which is perpendicular to the plane of the linear bearing thus allowing for the automatic leveling of the probe array 140 whereby the flat bottom surfaces of the array 140 and flanges 142 and 144 are maintained parallel to the adjacent underlying surface (not shown).

Illustrated in FIGS. 12 and 13 are still another embodiment of this invention in which one end of a cantilevered arm 160 supports an aerodynamically floating flange 162 which in turn supports and maintains a probe 164 at a constant distance from the surface of a recordable or prerecorded information cylinder 166. The end of cantilevered arm 160 opposite the flange 162 is pivotably supported by pivot pin 168 which extends through one end of arm 160 and the bifurcated upper section of pylon 170. Pin 168 allows the opposite end of arm 160 to freely move in a vertical direction. Pylon 170 is attached to a support pedestal 174 comprising a micrometer translating screw. Aerodynamically floating flange 162 contains a gas passageway 176 which is connected at the upper end to a source of compressed gas (not shown). The lower end of gas passageway 176 is open to allow gas to be ejected downwardly against the surface of cylinder 166. By simply altering gas pressure (which affects gas flow rate) to achieve the desired equilibrium distance between aerodynamically floating flange 162 and the surface of recordable or prerecorded information cylinder 166, a constant distance can be maintained for reading or recording. Cylinder 166 can be any suitable member such as a magnetically recordable member, optically recordable member, or electrophotographically recordable member. Such recordable materials and the like are well known in the art. An especially desirable write head 164 is one that emits a focused imaging beam of activating radiation from a source such as a light emitting diode which requires accurate constant spacing to position the focal point of the beam at exactly the desired location in the cylinder 166, for example at the outer surface of a thin charge generating layer of an electrophotographic recording member.

In FIG. 14, another embodiment of this invention is shown which utilizes a mechanical source of bias instead of gravity against which the aerodynamically floating device works. More specifically, a floating flange 180 is supported by a linear bearing 182 which is in turn supported by frame 184. Linear bearing 182 allows floating flange 180 to horizontally move toward or away from the vertical surface of a member 186. Member 186 may be any suitable media such as a photoreceptor, optical disk, magnetic storage device, and the like. A read or write head 188 is supported by flange 180. Floating flange 180 is biased toward member 186 by coil spring 190. Compressed gas is fed to passageway 192 through flexible feed line 194. The various components may be moveable in the directions shown by the arrows.

In FIG. 15, another embodiment of this invention is shown which also utilizes a mechanical source of bias instead of gravity against which the aerodynamically floating device works. More specifically, a floating flange 196 is supported by double cantilevered springs 198 which is in turn supported by arm 200. Double cantilevered springs 198 allow floating flange 196 to vertically move toward or away from the horizontal surface of a member 202. Member 202 may be any suitable media such as a photoreceptor, optical disk, magnetic storage device, and the like. A read or write head 204 is supported by flange 196. Floating flange 196 is biased toward member 202 by double cantilevered springs 198. Compressed gas is fed to passageway 206 through flexible feed line 208. Read or write head 204 and flange 196 may be moveable in the direction shown by the arrow. Not only does the use of double cantilevered springs 198 allow floating flange 196 to vertically move toward or away from the horizontal surface of a member 202, the double cantilevered springs 198 also maintains the flat lower surfaces of floating flange 196 and head 204 parallel to the adjacent upper surface of member 202.

The contactless constant distance scanner system of this invention in one embodiment detects charge deficient spots in electrostatographic members such as xerographic photoreceptors at a high speed. Large area scans, e.g. of a one pitch photoreceptor is feasible in a reasonable time vs. 1 cm² with a stylus scanner. The results provided by the high speed scanner system are highly reproducible and the number of point like defects increase in magnitude and number as the charging level is increased. Charge associated with charge deficient spots for a photoreceptor can be detected with one embodiment of the system of this invention, without any need for taking into account probe distance variations. This number correlates well with photoreceptor gradings. Statistical measures produced by the contactless constant distance scanner system of this invention also indicate photoreceptor quality. Values for the higher order moments of the potential fluctuations on the photoreceptor surface indicate the number and magnitude of charge deficient spots. A poor quality photoreceptor has large higher moments. Higher order moments are a well known statistical tool.

Electrophotographic (e.g. photoreceptor) flexible belt, rigid drum and flat plate imaging members are well known in the art. They may comprise one or more electrically operative layers usually supported on a substrate. Typical examples of photosensitive members having at least two electrically operative layers including a charge generator layer and charge transport layer are disclosed in U.S. Pat. No. 4,265,990, 4,233,384, 4,306,008, 4,299,897 and 4,439,507. The disclosures of these patents are incorporated herein in their entirety.

Members of any suitable configuration such as belt and drum shaped members may be evaluated, imaged, read or otherwise processed with the aerodynamically floating constant distance device of this of this invention. Aerodynamic floating constant distance devices are an excellent robust solution for maintaining constant distance between a device and a flat or cylindrical surface. The aerodynamically floating constant distance device system of this invention substantially reduces variations in device to member surface distance compared to a device at a fixed position and enables excellent reproducibility. Floating device positioning is insensitive to all major operating parameters and external conditions. The passive nature of the system of this invention removes the need for expensive active control equipment. It should be understood that a capacitive charge sensitive probe used for detecting charge deficient spots is just one example where aerodynamic floating can be helpful. Other measurements or processes requiring distance control can also use the same aerodynamic floating solution. It is also possible to maintain controlled distance between any array of probes or other devices by utilizing aerodynamic floating elements on both ends of an array or parallel to the sides of an array. The strength of the aerodynamic force acting between the floating device and the underlying surface and the equilibrium distance between the bottom of a device and the underlying surface will in general depend on the size of the opening through which the gas is passed, the external dimensions of the adjacent surface of the aerodynamic floating device, and the gas pressure. All these parameters may be utilized to optimize the aerodynamic floating device for a given application.

The scanning system of this invention may also be utilized to scan and digitize electrostatic latent images carried by imaging members. The electrostatic latent images may be formed on the imaging members by any suitable technique. Typical techniques for forming electrostatic latent images include, for example, electrophotographic processes and electrographic methods. In electrophotographic processes, a photoconductive imaging member is uniformly charged in the dark and thereafter exposed to activating radiation in image configuration thereby selectively discharging the photoreceptor to form the electrostatic latent image. The photoconductive imaging member may be of any suitable type comprising photoconductive material that is sensitive to activating radiation such as infrared radiation, visible light, X-rays, ultraviolet radiation, and the like. Electrographic latent images are formed on dielectric imaging members using suitable imagewise charging devices such as shaped electrodes, styli, stencils, ion streams and the like. The electrostatic latent image (e.g., comprising a pattern of charged areas and areas having little or no charge) is scanned and converted to digital signals by the scanning system of this invention. The digitized signals representative of the electrostatic latent image may be stored and subsequently used for any suitable purpose such as producing a hard copy for diagnostic purposes in case of X-ray imaging, processing with pattern recognition software, detection of image defects, electronic manipulation, and the like.

PREFERRED EMBODIMENT OF THE INVENTION

A number of examples are set forth hereinbelow and are illustrative of different compositions and conditions that can be utilized in practicing the invention. All proportions are by weight unless otherwise indicated. It will be apparent, however, that the invention can be practiced with many types of compositions and can have many different uses in accordance with the disclosure above and as pointed out hereinafter.

EXAMPLE I

A drum and CDS probe scanning system similar to that schematically presented in FIGS. 1 and 2 was used to compare fixed probe performance to aerodynamically floating probe performance. When the CDS scanner was operated in a testing configuration with a probe that was rigidly fixed during data acquisition (no aerodynamic float), the photoreceptor mounted on cylindrical drum was rotated under the probe as scanning progresses (see FIG. 1). Despite precision machining, a drum having a nominal diameter of 5 inches still retained a slight eccentricity of approximately ±25 $\mu$m. Since the gap between the probe and imaging surface of the photoreceptor was approximately 100 $\mu$m, this implied variations of ±25 percent. To be useful as a tool for quality control, it was essential that the aerodynamic floating device be able to maintain a constant probe to photoreceptor sample distance regardless of small eccentricities of the support drum. The aerodynamic floating probe device must also be able to adapt to changing surface features on the photoreceptor sample itself. Two experiments were conducted to illustrate how well the aerodynamic floating device of this invention adapts to these conditions. In the first, the ability of aerodynamic floating device to adapt to the eccentricity of the mounting drum was examined. The aerodynamic floating device comprising the flange, probe and movable portion of the linear bearing secured to the flange had a mass of about 50 grams. The flange contained a 1.5 millimeter diameter passageway extending perpendicular to the surface of the drum. The upper end of the passageway was connected by flexible tubing through a pressure regulator to a source of compressed air. The bottom surface of the flange was arcuate and parallel to the surface of the drum. This bottom surface of the flange had a surface area of about 1.6 square centimeters. The dimensions of a horizontal cross section of the flange was 1.27 centimeters by 1.27 centimeters. The aerodynamic floating device was positioned over the mounting drum with no photoreceptor sample in place, and equilibrium distance between the bottom of the probe and the surface of drum was measured while air flowed through the passageway toward the drum surface at a pressure of 28 lb/square inch, or 2 kg/cm². The drum was rotated to a new angular position and new probe to drum distance measurements were taken when the system again reached equilibrium. To compare the relative advantages of aerodynamic floating versus a fixed level probe, probe to drum distances were also measured with a probe held by a stop screw approximately 90 micrometers above the surface of the drum. The results of this experiment are illustrated in FIG. 4. The eccentricity of the drum was readily apparent from the measurements taken without the use of aerodynamic floating. The average equilibrium distances were found to be 54 μm and 93 μm for the measurements taken with aerodynamic floating (see dashed line in A) and without aerodynamic floating (see dashed line in B), respectively. It should be noted that distances measured when using a fixed level probe can be changed by a constant vertical shift simply by moving the stop screw which holds the probe in place. Probe to drum distance variations of ±20 μm were observed without aerodynamically floating positioning whereas variations of only ±3.5 μm were observed with the aerodynamic floating system active. While this data is for illustrating the merits of aerodynamic floating, it was collected with a mounting drum in a static configuration. When the drum 14 was moved to a new angular position to acquire a new measurement, the probe was allowed sufficient time (seconds) to come to a new equilibrium position. In an operational scenario, the drum rotates and allows only a limited amount of time (fractions of a second) for the aerodynamically floating positioning system to compensate for changing surface features of the photoreceptor sample. New problems may arise when measurements are taken with the drum in a dynamic configuration rather than a static one. To illustrate the performance of the aerodynamic floating system of this invention in a dynamic situation, the drum was set to rotate with a surface speed of 15 inches/sec, as in a typical test operation. A signal was applied to the rotating drum, and the corresponding signal induced in the probe was monitored using an oscilloscope. The resulting trace on the oscilloscope was transferred to Polaroid® film. The capacitance reading at a known drum position was measured with a capacitance bridge, and the corresponding voltage at the same spot was physically measured from the Polaroid film. Since voltage is proportional to capacitance, these measurements provided a benchmark to determine capacitance at other positions on the drum. By physically measuring the Polaroid® film and using ratios with the known benchmark, capacitances were calculated for other angular positions of the drum. The measurements obtained using this method are also illustrated in FIG. 4. As with the data obtained with the drum in a static configuration, the rotating drum showed an average probe to drum distance of approximately 53.6 μm for the aerodynamic floating system of this invention (see solid line in A), which differs by only 0.7 percent from the measurements taken from the static drum. The rotating drum also showed the same distance variations of 3.5 μm previously observed in the static configuration. Results of a fixed probe without aerodynamic floating is represented by the solid line in B of FIG. 4. The agreement between measurements taken from the mounting drum 14 in static and rotating (dynamic) configurations implies that drum rotation provides no impediment to accurate distance control with the aerodynamic system of this invention.

EXAMPLE II

All of these measurements were made in Example I were with the probe positioned over an area of a bare supporting drum, with no photoreceptor in place. The imaging surface of a photoreceptor is less uniform than the support drum surface and this non-uniformity can potentially present a substantial obstacle to obtaining reproducible positioning for ordinary fixed level probes. To demonstrate that aerodynamic floating can accurately position a probe over a photoreceptor sample, a conventional belt photoreceptor sample was attached to the mounting drum as it would be during normal scanner operation, and probe was moved to a position over the sample. The thickness of the photoreceptor belt was 100 micrometers. Because photoreceptors have a different dielectric strength than air, the probe was recalibrated. In Example I, only an air gap existed between the probe and the mounting drum, allowing the distance to be calculated relatively easily. When a photoreceptor was mounted on the mounting drum, the gap between the probe and ground plane of photoreceptor changed to one partially filled with a dielectric. This required correcting the 1/C versus d curve for photoreceptor capacitance. The correction is straightforward and fundamentally involves subtracting the dielectric thickness of the photoreceptor (e.g. 9 μm) from the distance determined using the calibration described above. While the equilibrium position over the photoreceptor was not identical to the equilibrium position over a bare mounting drum, the difference was small (about 5 μm), and the variation with position is very similar. The difference in equilibrium distances between photoreceptor and the bare drum may be due to small play of the linear bearing as it is of the same order as the error of 2.5 μm obtained from two successive measurements. Under all conditions, the equilibrium position of the scanner probe showed only minor variations which were substantially smaller than variations measured when using only a fixed level probe. Drum rotation had no significant effect on equilibrium position. While equilibrium distance appeared to change when the probe was positioned over the photoreceptor, the variations in the distance were very small, and comparable to those observed under other operating conditions of the aerodynamic floating system of this invention. In general, the aerodynamic floating system of this invention surprisingly showed a remarkable independence from all important operating parameters.

Although the invention has been described with reference to specific preferred embodiments, it is not intended to be limited thereto, rather those having ordinary skill in the art will recognize that variations and modifications may be made therein which are within the spirit of the invention and within the scope of the claims.

What is claimed is:

1. A contactless system comprising
   an aerodynamically floatable device,
   a member having an outer surface adjacent to and spaced from the aerodynamically floatable device,
   a support mechanism adapted to support the aerodynamically floatable device for free movement in a plane toward and away from the outer surface of the member,
   the aerodynamically floatable device having a side adjacent to, spaced from, parallel to and facing the outer surface of the member,
   the aerodynamically floatable device also containing at least one passageway for directing at least one stream of pressurized gas from the side of the aerodynamically floatable device toward the outer surface of the member with sufficient pressure to maintain the aerodynamically floatable device a constant equilibrium distance from the outer surface of the member.

2. A contactless system according to claim 1 wherein the movement of the aerodynamically floatable device toward and away from the outer surface of the member is in a vertical direction.

3. A contactless system according to claim 1 wherein the support mechanism includes a linear bearing to constrain the aerodynamically floatable device to free movement toward and away from the outer surface of the member.

4. A contactless system according to claim 3 wherein the aerodynamically floatable device is freely rotatable on an axis perpendicular to the plane of free movement for leveling when gas is directed from the side of the aerodynamically floatable device toward the outer surface of the member.

5. A contactless system according to claim 1 wherein the support mechanism includes a cantilevered arm having a free end, the free end supporting the aerodynamically floatable device.

6. A contactless system according to claim 1 wherein the side of the aerodynamically floatable device and the adjacent outer surface of the member have an arcuate shape.

7. A contactless system according to claim 1 wherein the side of the aerodynamically floatable device and the adjacent outer surface of the member are flat.

8. A contactless system according to claim 1 wherein the aerodynamically floatable device includes a capacitive probe.

9. A contactless system according to claim 8 wherein the capacitive probe is a probe array, the aerodynamically floatable device being rotatable to allow a plurality of passageways to align the side of the aerodynamically floatable device adjacent to, spaced from, parallel to and facing the outer surface of the member.

10. A contactless system according to claim 1 wherein the support mechanism adapted to support the aerodynamically floatable device includes double cantilevered springs disposed to maintain the side parallel to the adjacent outer surface of the member.

11. A contactless system according to claim 1 wherein the aerodynamically floatable device is spring biased toward the outer surface of the member, the outer surface being in any angular position.

12. A contactless system according to claim 1 wherein the aerodynamically floatable device contains a plurality of passageways for directing streams of a gas from the side of the aerodynamically floatable device toward the outer surface of the member with sufficient pressure to maintain the aerodynamically floatable device a constant equilibrium distance from the outer surface of the member.

13. A contactless system according to claim 1 wherein the aerodynamically floatable device is spring biased toward the outer surface of the member.

14. A contactless system according to claim 13 wherein the aerodynamically floatable device is movable in a vertical direction.

15. A contactless system according to claim 13 wherein the aerodynamically floatable device includes an electrostatic probe.

16. A process according to claim 13 wherein the aerodynamically floatable is movable in a substantially vertical direction.

17. A contactless system according to claim 1 wherein the side of the aerodynamically floatable device and the outer surface of the member are curved, the side of the aerodynamically floatable device being concave and the outer surface of the member being convex.

18. A contactless system according to claim 1 wherein the member is a rotatable drum.

19. A contactless system according to claim 18 wherein the support mechanism includes a linear bearing to constrain the aerodynamically floatable device to free movement in a direction substantially normal to an imaginary tangent to the surface of the drum.

20. A contactless system according to claim 18 wherein the passageway extends through the aerodynamically floatable device and is disposed to direct the stream of pressurized gas in a direction substantially perpendicular to an imaginary tangent to the surface of the drum.

21. A contactless system according to claim 18 wherein the support mechanism is also disposed to move the aerodynamically floatable device parallel to an imaginary axis of the drum.

22. A contactless system according to claim 21 wherein the support mechanism also comprises a stepper motor and a micrometer screw to move the aerodynamically floating device parallel to an imaginary axis of the drum.

23. A contactless system according to claim 22 wherein the aerodynamically floating device supports an electrostatic probe and the stepper motor and a micrometer screw is adapted to move the aerodynamically floating device and probe parallel to the imaginary axis of the drum from a first scan line position to a new scan line position.

24. A contactless system according to claim 23 wherein the support mechanism is adapted to maintain the aerodynamically floating device stationary in a scan line position while the drum is rotating during acquisition of data by the probe.

25. A contactless system according to claim 1 wherein the aerodynamically floating device is supported on a first end of a cantilevered arm having a first end and a second end, the second end of the cantilevered arm is pivotably supported by pivot pin which extends through the second end of arm and through a bifurcated upper section of a pylon, and the pylon is attached to a support pedestal comprising a micrometer translating screw.

26. A contactless system according to claim 1 wherein the member is a magnetically recordable member.

27. A contactless system according to claim 1 wherein at least one passageway is connected by a flexible feed line through a pressure regulator to a source for compressed air.

28. A contactless system according to claim 1 wherein the aerodynamically floatable device comprises a write head disposed to emit a focused imaging beam of activating radiation at the member.

29. A contactless system according to claim 1 wherein the aerodynamically floating device has opposite ends, an array of probes between the ends and a passageway at each of the ends for directing pressurized gas toward the outer surface of the member to maintain the side of the aerodynamically floatable device adjacent to, spaced from, parallel to and facing the outer surface of the member.

* * * * *